United States Patent [19]

Bachman

[11] Patent Number: 4,782,282

[45] Date of Patent: Nov. 1, 1988

[54] CAPACITIVE-TYPE SEED SENSOR FOR A PLANTER MONITOR

[75] Inventor: Wesley J. Bachman, Auburn, Ill.

[73] Assignee: Dickey-john Corporation, Auburn, Ill.

[21] Appl. No.: 883,558

[22] Filed: Jul. 9, 1986

[51] Int. Cl.$^4$ .............................................. G01R 27/26
[52] U.S. Cl. ............................ 324/61 R; 324/61 QS;
324/714; 340/684
[58] Field of Search ........... 324/61 QL, 61 QS, 61 R,
324/71.4; 340/684; 111/1

[56] References Cited

U.S. PATENT DOCUMENTS

| | | | |
|---|---|---|---|
| 2,094,351 | 9/1937 | Draper | 177/311 |
| 2,490,679 | 12/1949 | Davidson | 192/130 |
| 2,646,559 | 7/1953 | Nutzler | 340/258 |
| 2,665,409 | 1/1954 | Rogers | 324/61 |
| 2,726,366 | 12/1955 | Rogers | 324/61 |
| 2,950,436 | 8/1960 | Butticaz et al. | 324/61 |
| 3,339,137 | 8/1967 | Perry | 324/61 |
| 3,340,400 | 9/1967 | Quittner | 250/219 |
| 3,390,577 | 7/1968 | Phelps et al. | 73/194 |
| 3,469,157 | 9/1969 | Rhodes | 317/246 |
| 3,500,366 | 3/1970 | Chensey et al. | 324/71.4 X |
| 3,593,128 | 7/1971 | Perry | 324/61 |
| 3,676,772 | 7/1972 | Lee | 324/41 |
| 3,697,972 | 10/1972 | Brown | 340/258 |
| 3,702,957 | 11/1972 | Wolfendale | 317/246 |
| 3,715,656 | 2/1973 | Hyde et al. | 324/61 |
| 3,774,238 | 11/1973 | Hardway, Jr. | 324/61 |
| 3,812,424 | 5/1974 | Abbe | 324/61 |
| 3,881,353 | 5/1975 | Fathauer | 73/194 A |
| 3,895,384 | 7/1975 | Fathauer et al. | 343/9 |
| 3,979,581 | 9/1976 | Reuland | 324/61 R X |
| 4,137,529 | 1/1979 | Anson et al. | 340/684 |
| 4,163,507 | 8/1979 | Bell | 221/2 |
| 4,223,751 | 9/1980 | Ayers et al. | 177/210 C |
| 4,239,010 | 12/1980 | Amburn | 111/1 |
| 4,240,528 | 12/1980 | Kraus | 187/52 |
| 4,246,469 | 1/1981 | Merlo | 235/92 |
| 4,288,741 | 9/1981 | Dechene et al. | 324/61 |
| 4,311,958 | 1/1982 | Aeppli | 324/61 |
| 4,333,096 | 6/1982 | Jenkins et al. | 340/684 |
| 4,560,923 | 12/1985 | Hanson | 324/61 QL |

Primary Examiner—Reinhard J. Eisenzopf
Assistant Examiner—Robert W. Mueller
Attorney, Agent, or Firm—Trexler, Bushnell, Giangiorgi & Blackstone, Ltd.

[57] ABSTRACT

A sensor apparatus for detecting a flow of material along a given path of travel by detecting a change in the dielectric properties of a portion of the path of travel as the material passes therethrough comprises one or more conductive, plate-like electrodes disposed adjacent the path of travel and generally defining a capacitor having the adjacent portion of the path of travel as a dielectric portion, such that the passage of material to be detected changes the dielectric constant, thereby changing the capacitance. A sensor circuit comprises a tuned circuit having the sensor electrode or electrodes being coupled in circuit therewith. The sensing circuit further comprises an oscillator circuit driving the tuned circuit at a predetermined frequency selected near the resonant frequency of the tuned circuit in the absence of material to be detected. The sensing circuit further includes an AM demodulator circuit coupled to the tuned circuit for developing a sensor circuit signal at a substantially constant level in the absence of material to be detected and a measurable change in signal level when the material to be detected is present.

24 Claims, 3 Drawing Sheets

U.S. Patent  Nov. 1, 1988  Sheet 1 of 3  4,782,282
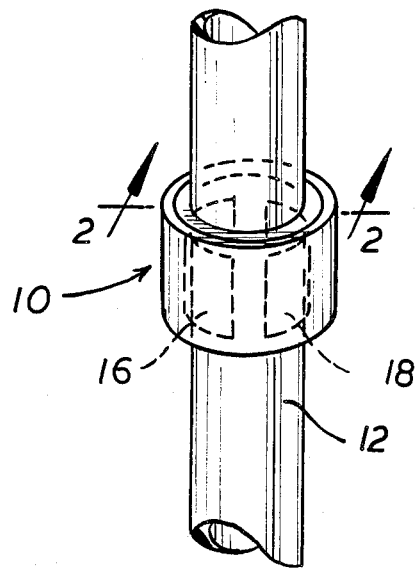
FIG.1
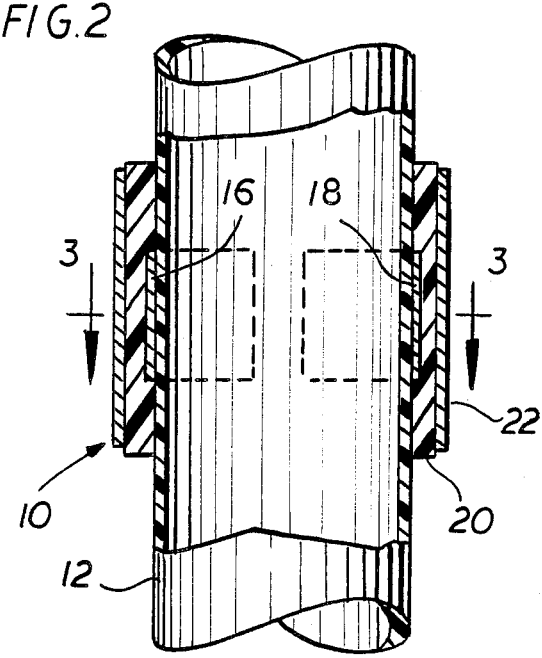
FIG.2
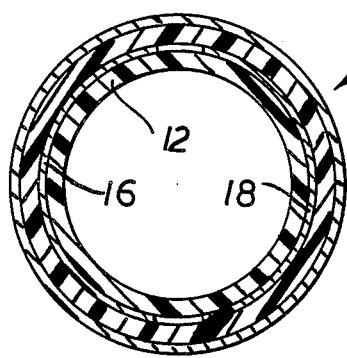
FIG.3
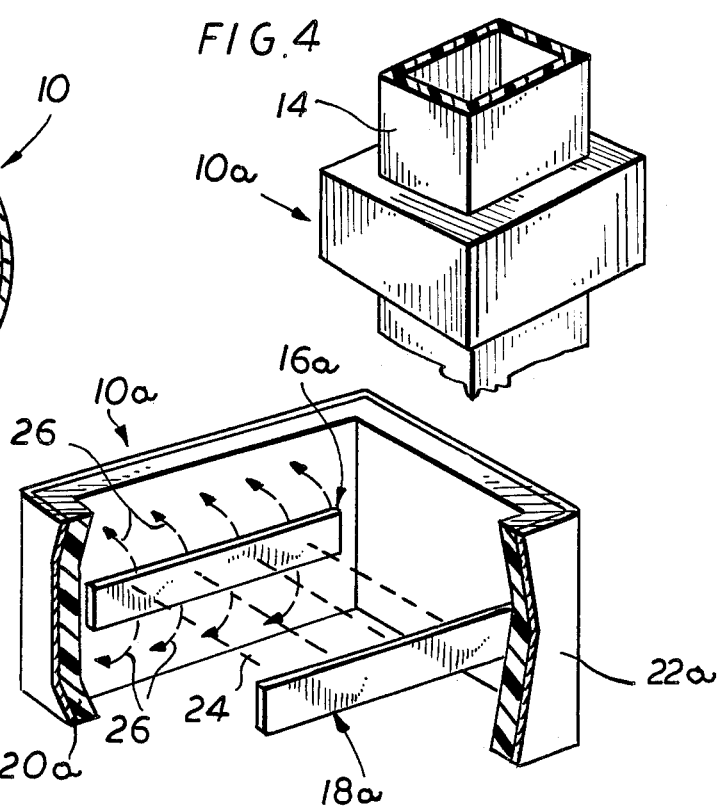
FIG.4
FIG.5

CAPACITIVE-TYPE SEED SENSOR FOR A PLANTER MONITOR

BACKGROUND OF THE INVENTION

The invention is directed generally to the material sensing arts and more particularly to a novel and improved sensor apparatus for detecting the flow of material along a given path of travel.

While the invention may be useful in connection with monitoring the flow of various materials, the description will be facilitated by reference to the particular problem of detecting the passage of a plurality of discrete articles, such as seeds in a field seed planter, along a given path of travel. For example, such monitoring is often desired at discharge tubes of the field seed planter where the seeds are discharged to the ground to be planted. It will be understood that the invention is not so limited, but may also find utility in connection with the monitoring of flow of materials of various types through tubes, conduits or other structures which define predetermined paths of travel through which such material or seeds or other discrete articles may travel or flow and be detected.

As is well known, a farmer engaged in mechanized planting of various seeds utilizes a planting machine pulled behind a tractor. Such planting machines usually include a plurality of spaced apart individual planting units which are supplied with seeds from one or more hoppers or containers so that a plurality of rows of seeds may be planted at one time. The prior art has provided a number of different seed sensing and/or monitoring systems for maintaining a count of the seeds planted by such a planting machine and for providing useful indications or read-outs such as seed population and the like to the farmer or machine operator.

In such systems, an individual sensing apparatus or device is generally associated with each of the seed planting units to provide an output signal in response to the passage of seeds therethrough. For relatively small and densely planted seeds such as vegetable seeds or the like, individual seeds may not be detected as such, but rather it may only be desired to detect the presence or absence of a flow of seeds being delivered. In this regard, the sensing apparatus or device is usually associated with a seed planting conduit or outlet chute of the planting unit through which the seeds travel immediately prior to being released from the machine to be planted. On the other hand, where relatively larger and less densely planted seeds such as corn or soybeans are being planted, it is usually desirable to maintain a count of the seeds planted by each unit so that seed population and other useful seed count-dependent information can be determined.

The prior art has developed a number of different approaches for the design and operation of such seed sensors. The earliest of these approaches utilized a sensitive mechanical switch having an actuator member placed in the flow path of the seeds within a seed chute or conduit. Hence, each seed passing through the conduit would strike the actuator member of the mechanical switch, causing the switch to momentarily switch between open circuit and closed circuit states or vice-versa to develop a corresponding electrical signal. Such sensor devices are shown, for example in U.S. Pat. Nos. 2,907,015 to Young, 3,527,928 to Ryder et al.; and 3,632,918 to Anson et al.

Another approach to seed sensing utilizes photoelectric or photosensitive devices to detect the passage of seeds through the tubes or chutes. In such an arrangement, a light source and a photoelectric or photosensitive device are placed in optical alignment at opposite sides of the seed chute or conduit. Hence, the passage of a seed through the conduit and between the light beam and photo sensitive device produces a characteristic output signal, which output signal can then be monitored or otherwise processed to detect the flow, and in some instances to count the seeds passing through the planting tube or chute. Such devices are shown, for example in U.S. Pat. Nos. 3,537,091 to Shenkenberg; 3,723,989 to Fathauer; and 3,974,377 to Steffen. These photosensitive seed sensing devices are the type most widely used in the art today and have enjoyed widespread acceptance and commercial success.

Yet another form of sensing device has been proposed which makes use of ultrasonic sensing apparatus. This apparatus sets up an ultrasonic wave or energy rather than light energy in the tube and operates to detect disturbances in this ultrasonic energy caused by the passage of seeds through the tube. Such an ultrasonic sensing apparatus is shown in U.S. Pat. No. 3,881,353 to Fathauer.

Yet another type of seed sensor utilizes microwave energy. This type of sensor provides a waveguide intersecting a portion of the path of travel of seeds for supporting the propagation of a standing wave pattern of microwave energy. Generally speaking, this apparatus detects disturbances in this standing wave pattern due to the passage of seeds through the seed conduit, and in particular through the portion thereof in which the waveguide is located. Associated circuitry is responsive to these disturbances or changes in microwave energy in the waveguide for determining the presence or absence of seeds, as well as in some instances for counting the seeds. One such microwave seed sensor apparatus is shown for example in U.S. Pat. No. 4,246,469 to Merlo, and another such microwave seed sensing apparatus is shown in U.S. Pat. No. 4,239,010 to Amburn.

The present invention is directed to yet another form of seed sensing device which makes use of the dielectric properties of seeds and/or other material or articles flowing along a path of travel to provide for detection of such seeds, material or other articles. Generally speaking, the present invention contemplates setting up an electromagnetic field transversely of the path of travel, such as in the seed chute or conduit and detecting changes in the electromagnetic field due to the passage of such seeds or other discrete articles or the flow of material therethrough.

More particularly, in a case of seeds or articles or materials having measurable dielectric properties, we have found that a sensor having primarily capacitive or capacitance-like properties may be utilized. More particularly, a pair of relatively simple and inexpensive conductive plates may be placed to either side of the path of travel, such as a seed conduit or chute. These plates generally define plates of a capacitor with the seed conduit portions therebetween comprising the dielectric portion of the capacitor. Hence, if an object or material of a different relative permittivity or dielectric property relative to air enters this field, the electric field state will be altered. The resulting alteration can be separated into both a tansient effect and steady state effect. We have found that the transient effect is generally much less pronounced than the steady state effect and of much shorter time duration.

Additionally, a capacitor or capacitive-type of sensor arrangement, as such, is capable of essentially two basic functions. Firstly, such a device may be utilized to transmit energy; and secondly, the device may be utilized to store energy. The first or energy transmission capability is generally utilized in coupling and bypass types of uses, while the second function is useful in applications such as filters, timing, phase shifting and resonant circuit type of applications. Various prior art sensing devices utilizing capacitive type sensors are also known. Such sensors are often utilized in steady state applications to detect the amount of moisture, or some other ingredient of a material, particularly in agricultural grain moisture tester devices. Such moisture testers are shown for example in U.S. Pat. Nos. 3,794,367 to Fathauer and 4,058,766 to Vogel et al.

The prior art capacitive-type sensor and detector arrangements have utilized a number of properties of capacitors and various circuit arrangements to achieve the desired sensing or detection functions. For example, in a resonant-type of circuit, detection or sensing often utilized the phase or frequency shifts observed in the circuit. Such phase or frequency shifts occur due to the entrance of articles or materials to be detected or sensed into the electromagnetic field of the capacitive-type sensor, thus changing the properties of this field, as well as the capacitance properties of the sensor element or arrangement. Such changes of a capacitance component in a resonant-type of circuit can be detected as changes in phase or changes in the resonant frequency of the circuit.

However, we have found that the measurement of such frequency shifts or changes essentially requires narrow band FM demodulation. While this approach is workable, it requires that the detection circuits track the frequency drift of an oscillator which drives the resonant circuit, of which the capacitive sensor forms a part. We have found, however, that the oscillator drift may be expected to be as much as 10 times the detector bandwidth, which makes the problem of tracking of frequency drift relatively difficult and expensive t accomplish.

We have also found with respect to phase shift detection that a phase demodulator having a relatively high Q is needed to obtain the required sensitivity. However, a high Q circuit inherently has a very narrow bandwidth which in turn requires that suitable tuning circuits be utilized. Alternatively, various noise reduction techniques and circuits may be utilized in order to maintain an adequate signal to noise ratio to compensate for lowered sensitivity of the circuit. However, this solution is generally very costly in terms of required circuit complexity and requires relatively substantial real time for the necessary signal processing. In many detection applications, especially in the sensing of seeds which are delivered at a relatively rapid rate in a field seed planter, this amount of time for signal processing is not available.

Advantageously, we have found that amplitude detection methods may be employed, utilizing a relatively lower Q than frequency or phase detection methods. Moreover, we have found that sensitivity may be readily increased by increasing the input drive level with little increase in total noise in such an amplitude detection arrangement. More particularly, we have found that utilizing a resonant circuit such as a singly tuned, magnetically coupled circuit permits a change in amplitude to be detected as a voltage measurement directly across the capacitive sensing element.

OBJECTS OF THE INVENTION

Accordingly, it is a general object of the invention to provide a capacitive-type of sensing apparatus for detecting the flow of material along a given path of travel.

A more specifice object is to provide a capacitive-type sensing apparatus in accordance with the foregoing object adapted to detect the passage of individual seeds along a seed delivery tube of a field seed planter.

A further object is to provide a capacitive-type sensor in accordance with either of the foregoing objects which utilizes amplitude detection as discussed above.

A related object is to provide a sensor apparatus in accordance with one or more of the foregoing objects which is relatively simple and inexpensive in its design and manufacture and yet highly reliable in operation.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 1 is a perspective view of a capacitive-type of sensor apparatus in accordance with one form of the invention, mounted to a generally cylindrical seed delivery tube or conduit;

FIG. 2 is a sectional view taken generally in the plane of the line 2—2 of FIG. 1;

FIG. 3 is a sectional view taken generally in the plane of the line 3—3 of FIG. 2;

FIG. 4 is a perspective view, similar to FIG. 1, of a capacitive-type sensor device mounted to a generally rectilinear tubular conduit;

FIG. 5 is an enlarged perspective view, partially broken away, illustrating further details of the sensor apparatus of FIG. 4;

DETAILED DESCRIPTION OF THE ILLUSTRATED EMBODIMENT

Figure 6:
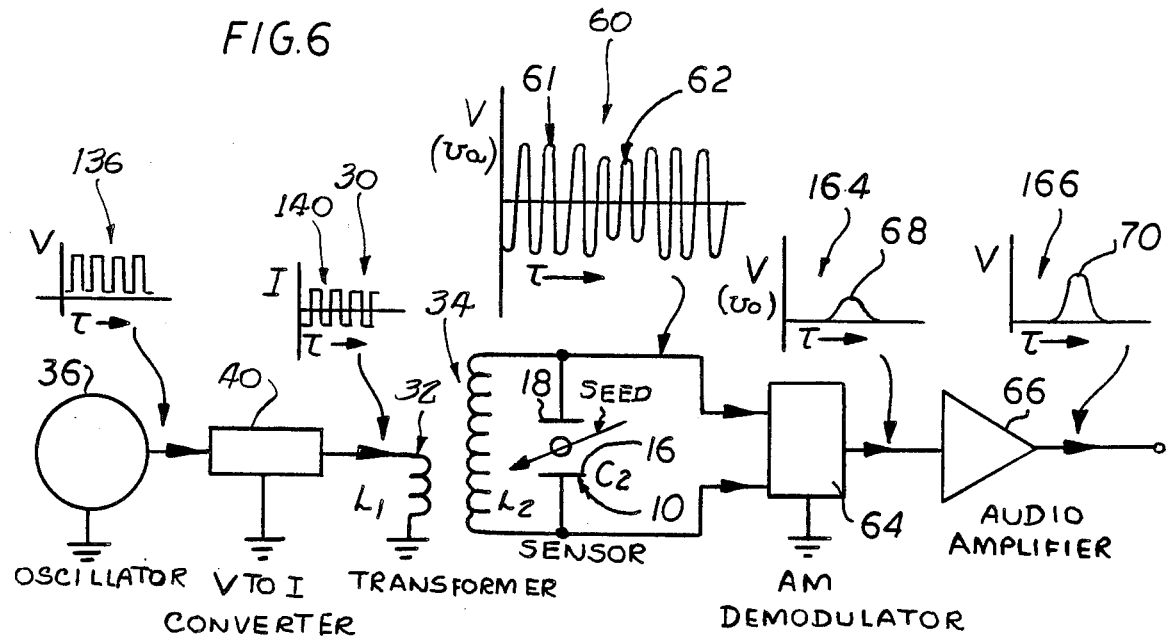
FIG. 6 is a block schematic circuit diagram of a sensing circuit in accordance with the invention, coupled in circuit with a capacitive-type sensor.

Referring to the drawings, and initially to FIGS. 1-5, the invention concerns a sensor apparatus for detecting a flow of material along a given path of travel. Such a sensor apparatus is designated generally be reference numeral 10. In the embodiment of FIGS. 1-3, the sensor apparatus 10 is associated with a generally circular or cylindrical tube 12 which defines the path of travel for material to be detected. On the other hand, in the embodiment of FIGS. 4 and 5, a similar sensor 10a detects material flowing along a path of travel defined by a tubular conduit 14, which is generally rectangular in cross-section. Other shapes or configurations of tubular conduits defining such a path of travel may be utilized without departing from the invention. Moreover, while the invention will be described hereinbelow with respect to detecting and preferably providing a signal suitable for counting discrete articles such as seed in a field seed planter, it will be understood that the invention is not so limited. In accordance with the invention, the sensor apparatus 10 or 10a operates by detecting the change in the dielectric properties of a portion of the path of travel defined by the conduit 12 or conduit 14 as the material or seed or other discrete object to be detected pass therethrough. For this purpose, the apparatus 10 or 10a comprises a capacitor or capacitive test cell defined by electrode means, here comprising two conductive, plate-like electrodes 16, 16a and 18, 18a which are disposed to either side of the path of travel and generally in alignment with each other. Hence, the portion of the path of travel running between these two plates comprises a dielectric portion of the capacitor thus defined. Accordingly, the passage of seeds or other material to be detected between these plates, 16, 16a and 18, 18a will change the dielectric properties or dielectric constant therebetween, thereby changing the capacitance across these plates. Other plate or electrode placements or configurations may be used for other applications without departing from the invention, including both single and multiple plate or electrode arrangements.

The plates in the embodiment of FIGS. 1–3 are generally curvilinear or semicircular in configuration to correspond to the curvature of the cylindrical tube 12. On the other hand, the plates 16a, 18a of the embodiment of FIGS. 4 and 5 are generally flat, planar members. Moreover, in each of the embodiments, the plates preferably extend substantially across the cross-sectional dimension of the path of travel in their dimension transverse to this path, but are relatively short in their dimension running along the path of travel, that is in the axial direction of the respective tubular conduits 12, 14. The tubular conduits 12 and 14 are preferably of an electrically nonconductive material, such as a suitable plastics material, so as to permit the desired electric field between the plates to be propagated therethrough.

In the embodiments illustrated, a quantity of nonconductive or insulating material 20, 20a surrounds the plates or electrodes 16, 18 and 16a, 18a and preferably the entire portion of the tube 12, 14 on which they are mounted. Preferably, this insulating protective material 20, 20a extends for some distance axially in either direction from the axial top and bottom edges of the respective plates. Additionally, a conductive exterior metallic shield member or portion 22, 22a preferably surrounds this insulating material 20, 20a to provide EMI/RFI shielding for the respective plates. Accordingly, this shield 22, 22a also extends axially for some distance beyond the respective top and bottom edges of the associated plates or electrodes. The shield 22, 22a may be a separate sheet of suitable conductive material or may be in the form of a foil or of a conductive coating suitably bonded or otherwise applied to the exterior surface of insulating material 20, 20a. In this regard, the plates 16, 18 or 16a, 18a may also be formed in any of the foregoing ways.

Consequently, and as best viewed in FIG. 5, the electric field lines 24 developed between plates 16, 16a and 18, 18a extends primarily across the path of travel between these two electrodes with edge field lines being substantially minimized and terminated, as indicated by the short arrows 26, by the shield 22 or 22a. Hence, the electric field for detection of material or seeds passing through the tubular conduit is confined essentially to the area between the two electrodes. Since the electrodes are relatively narrow in the axial direction, it is possible to discriminate between relatively closely spaced seeds or other objects passing therebetween, if it is desired to maintain a count of such seeds or other objects.

Figure 7:
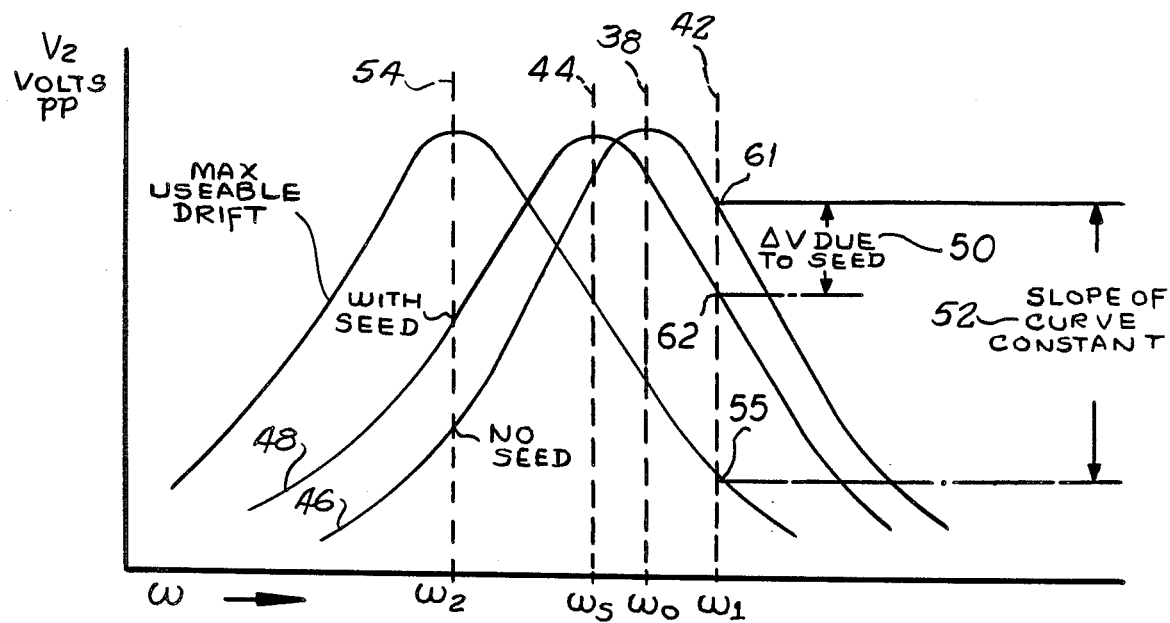
FIG. 7 is a graphic representation of signals developed in the circuit of FIG. 6.
Figure 8:
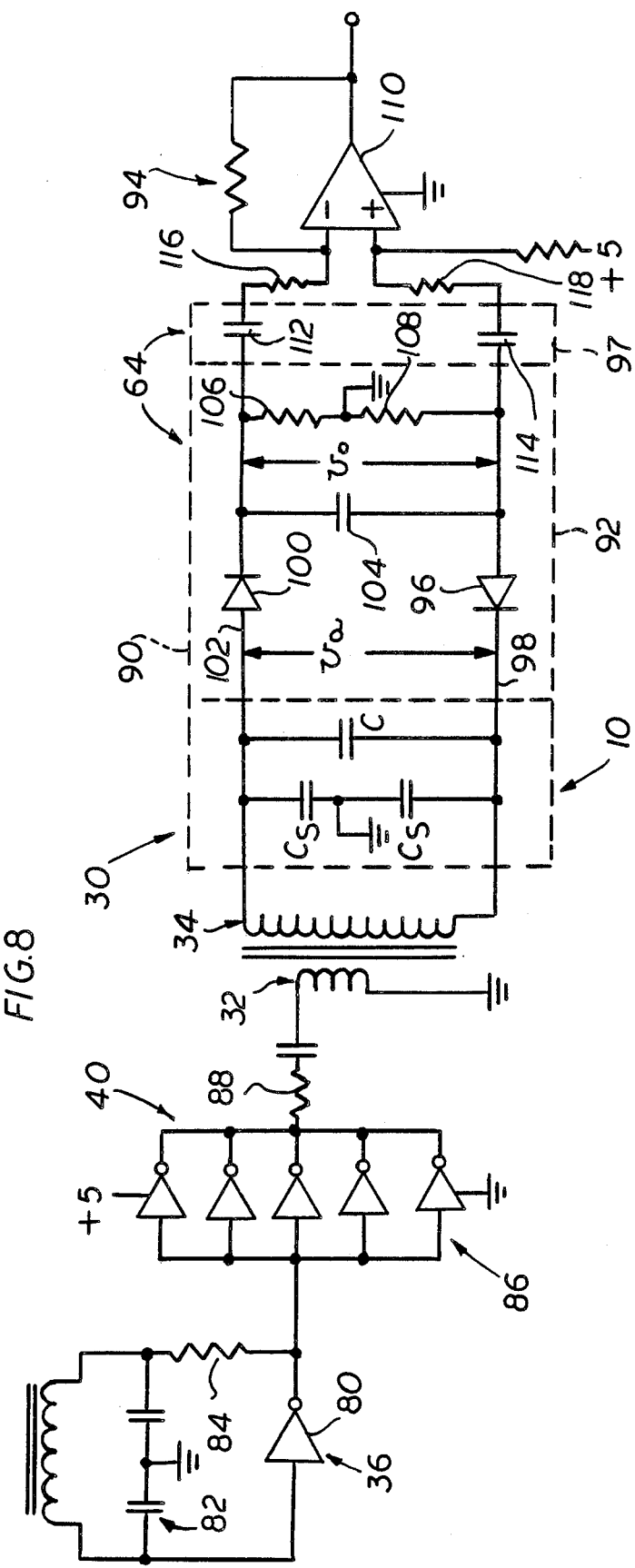
Fig. 8 is a detailed circuit schematic showing a preferred form of the details of the circuit of FIG. 6.

Referring now also to FIGS. 6–8, a novel sensor circuit in accordance with the invention, for use in connection with the sensor apparatus 10, 10a of FIGS. 1–5, is designated generally by the reference numeral 30. This circuit is shown in block schematic form in FIG. 6 and in detailed circuit schematic form in FIG. 8. Referring initially to the block diagram of FIG. 6, the sensor apparatus or assembly 10 (or 10a) is schematically indicated a a capacitor C2 coupled in circuit with this sensor circuit 30. More particularly, the sensor circuit 30 comprises a tuned circuit, and preferably a singly tuned, magnetically coupled circuit having a primary circuit portion or coil 32 (also designated Ll) and a secondary circuit portion or coil 34 (also designated L2). The sensor electrodes 16, 18 (or 16a, 18a) are coupled in electric circuit across or in parallel with the secondary coil 34. The primary coil 32 is driven at a predetermined frequency by an oscillator 36. This predetermined frequency is selected near the resonant frequency of the singly tuned circuit in the absence of a seed, or other material or object to be detected, between the plates 16, 18. This resonant frequency (wo) is indicated on the graph of FIG. 7 at reference numeral 38.

In accordance with the preferred form of the invention illustrated, an additional voltage-to-current (V to I) converter 40 is also provided intermediate the oscillator and the transformer primary 32 so as to provide a current source drive for the primary. This makes the primary current independent of changes in the load on the secondary. In this regard, the voltage against time output of oscillator 36 is shown graphically in a small graph 136 above oscillator 36. Similarly, the voltage-to-current converter output current wave form is indicated graphically at 140 adjacent the V to I converter 40. Preferably, the transformer primary inductance is on the order of 10 nanohenries, which at an operating frequency on the order of 5 MHz, exhibits a reactance of about 0.3 ohms. Other values may be used without departing from the invention. For a fuller analysis of the operation of a singly tuned, magnetically coupled circuit, reference is invited to the textbook *Analysis of Electric Circuits*, Brenner & Javid, McGraw-Hill Book Company, Inc., 1959 ed., pages 608–611.

As mentioned hereinabove, the oscillator frequency is chosen somewhat offset, and for reasons that will be explained later, somewhat above, the circuit resonant frequency 38. This oscillator frequency (wl) is indicated in FIG. 7 at reference numeral 42. The material to be detected, which in the illustrated embodiment is a discrete article having dielectric properties, such as a seed, will change the dielectric constant and hence capacitance of sensor 10 or 10a (C2). More particularly, a seed has a dielectric constant generally greater than air, and the capacitance of the sensor 10 or 10a is of course directly proportional to this dielectric constant. Hence, the resonant frequency of the circuit will shift downwardly somewhat due to the presence of a seed between plates 16, 18 as diagrammatically indicated in FIG. 6. Referring to Fig. 7, this shifted resonant frequency is indicated generally at reference numeral 44 (wS).

Referring more particularly to FIG. 7, the graph represents the radian frequency (w) against the peak-to-peak volts (V2 VOLTS PP) across the sensor capacitor 10 or 10a (C2). Accordingly, the change in voltage due to the presence of a seed can be expressed in the graph of FIG. 7 as the voltage difference between the peak-to-peak value at operating frequency 42 (wl) along the two frequency-voltage curves formed about resonant frequencies 38 and 42 (wO and wS). In this regard, the voltage-frequency curve with no seed present is indicated at reference numeral 46 (NO SEED), while the voltage-frequency curve with the seed present is indicated at reference numeral 48 (WITH SEED). The change in voltage due to the presence of the seed is therefore as indicated by the double arrows 50.

On the foregoing graph, it will now be appreciated that the selection of the operating frequency somewhat removed from, and preferably higher than the resonant frequency of the circuit is such as to place the operation of the circuit in a substantially linear or constant slope portion of the frequency-to-voltage curve, as indicated by the double arrows 52. Hence, the reason for this operating frequency selection is to 25. achieve operation in this substantially linear area for a material such as a seed having a dielectric constant greater than air. In this regard, it will be appreciated that operation could also be selected at some frequency point less than the resonant frequency 38 which would merely reverse the sense of the observed voltage variation or change. Moreover, the selected operating frequency 42 (wl) permits a considerable range of change in dielectric constant while remaining in the linear region, as indicated for example in the graph of FIG. 7 at reference numeral 54 (w2). This latter resonant frequency 54 (w2) indicates approximately the maximum usable "drift" or variation in resonant frequency due to presence of material or an object or seed, where the slope of the curve ceases to be substantially linear or constant, at operating frequency 42 (wl), as indicated at reference numeral 55.

This choice of operation somewhat away from the resonant frequency also allows for some shift in the resonant frequency over a period of operation. Such a shift may occur due to wear or other slight variations in the components due to environmental changes or the like, or due to the build-up of some amount of foreign materials such as dirt or other debris in or around the sensor apparatus 10 or 10a over a period of operation. It will be noted that operation at the resonant frequency is generally not desired since the slope of the curve is essentially zero at the resonant point, such that any shifts in the resonant frequency might cause a change in the signal sense as the signal shifts to one or other side of the zero slope portion of the curve.

The voltage change or variation due to passage of a seed, indicated by reference numeral 50 in FIG. 7, is also experienced as a change in the net amplitude of the oscillatory or sinusoidal waveform across the secondary 34, as indicated at 62 in the small graph 60 thereabove in FIG. 6. This graph 60 illustrates the voltage plotted against a time axis. It will be noted that in the illustrated embodiment, the effect of the seed is to momentarily decrease the peak-to-peak amplitude 61 of the voltage V, as indicated at reference numeral 62. The two peak-to-peak voltage reference points 61 and 62 are also indicated on the graph of FIG. 7. Hence, the effect of passage of the seed is essentially to modulate the amplitude of the oscillatory voltage across the secondary.

Accordingly, and in accordance with the invention, this change in voltage is detected by an amplitude modulation (AM) demodulator circuit 64 (AM DEMODULATOR). This amplitude demodulation has the effect of demodulating the change in signal level 50 as a momentary change or "hump" in an otherwise substantially constant voltage at some given reference level, as indicated generally at 68 in the small graph 164 adjacent AM demodulator 64. An additional audio amplifier 66 may also be utilized if desired, to amplify this voltage transient or hump 68 to some desired level 70 as indicated in corresponding graph 166.

Hence, the AM demodulator circuit is coupled essentially across the secondary 34 so as to develop a sensor circuit signal as indicated in graph 164 at a substantially constant level vo) in the absence of material such as a seed to be detected between the plates or electrodes 16, 18. However, this circuit produces a measurable change 68 in this signal level when the material or seed is present between electrodes or plates 16, 18.

Referring now also to FIG. 8, the circuits of FIG. 6 are indicated in detail in circuit schematic form. The oscillator circuit 36 will be seen to comprise a feedback type of oscillator comprising an active device 80 which has a 180 degree phase shift and a capacitively tapped tank circuit 82 which produces an additional 180 degrees to give the 360 degrees required for oscillatory operation. A resistor 84 allows both ends of the tank to oscillate sinusoidally, which contributes to increased stability of the oscillator circuit by reducing the harmonic content. A buffer circuit 86 coupled with the output of the oscillator 36 produces the square wave form of output as shown at 136 in FIG. 6. As mentioned above, the inductance of primary coil 32 is such that its reactance is about 3 ohms at the frequecy of operation of the oscillator. Hence, the majority of the voltage appears across coupling resistor 88 which essentially performs the voltage-to-current conversion function. As also mentioned above, this current-driving of the primary 32 makes the primary current substantially independent of changes in the load on the secondary.

The capacitive-type sensor 10 or 10a is coupled across the secondary 34 as previously noted. In FIG. 8, this capacitance has been indicated by the capacitance C across the plates or electrodes 16, 18 or 16a, 18a and the stray capacitance values Cs between the respective plates 16, 18 or 16a, 18a and the grounded shield 22 or 22a. It will be also noted that the voltage across the secondary 34 is here indicated by va, the same designation also being applied to the curve 60 of FIG. 6.

In the illustrated embodiment, the AM demodulator circuit comprises a rectifier circuit 90 coupled with the secondary 34 and a low pass filter circuit 92 coupled with the rectifier circuit 90. An additional amplifier circuit 94 coupled with the latter low pass filter circuit completes the AM demodulator circuit.

In the illustrated embodiment, the rectifier circuit 90 comprises a first diode 96 having a cathode 98 coupled with one side of the secondary and a second diode 100 having an anode coupled with the opposite side of the secondary 34. The low pass filter circuit 92 is coupled across the respective opposite poles of the diodes; that is, across the cathode of diode 100 and anode of diode 96. This low pass filter circuit comprises a capacitor 104 coupled across the respective anode of diode 96 and cathode of diode 100 and resistive means comprising a pair of resistors 106, 108 coupled respectively intermediate the two sides of the capacitor 104 and a reference voltage for establishing a DC bias point for the secondary 34, and together with the capacitor forming the low pass filter circuit 92. In the illustrated embodiment, the voltage reference or DC bias point is established at circuit ground.

Preferably, the AM demodulator circuit also includes a DC removal circuit 97 coupled intermediate the low pass filter and amplifier circuit 94. In this regard, the amplifier circuit 94 illustrated comprises a difference-type amplifier 110 having two inputs, an inverting input and a non-inverting input. The illustrated DC removal circuit 97 comprises a pair of capacitors 112, 114 coupled respectively in series circuit intermediate the low pass filter 92 and the respective inputs of the difference-type amplifier 110.

More specifically, the capacitor 112 is coupled in series intermediate the cathode of diode 100 and the inverting input of amplifier 110, while capacitor 114 is coupled in series between the anode of diode 96 and the non-inverting input of amplifier 110. Additional series-coupled resistors 116 and 118 are also provided intermediate the respective capacitors 112 and 114 and their associated inputs of amplifier 110. These coupling capacitors 112 and 114 remove the DC pedestal or DC bias level of the circuit, allowing the difference amplifier to respond only to the change in voltage due to the passage of a seed, for example, as illustrated at reference numeral 68 in the diagram 164 of FIG. 6. Together with the differential amplifier input resistance, these capacitors also provide a convenient reference for the demodulated output. Other specific circuit configurations (e.g., a single-ended demodulator) may be utilized without departing from the invention.

It should be noted that the choice of the RF value of operation of oscillator 36 is not critical to the operation of the circuit. While a frequency on the order of 2 MHz would be suitable, somewhat higher frequencies would permit some reduction in capacitor values in the circuit, which generally results in some cost savings. However, adequate sensitivity is present in the circuit in accordance with the invention, such that some latitude is permitted in selecting an operating frequency, as desired for other cost or convenience considerations. It should be recognized in this fegard that the resonant frequency is essentially inversely proportional to the square root of the product of the inductance of the secondary 34 and capacitance of the sensor 10.

For purposes of illustrating one particular form or embodiment of the invention, the following values or dimensions have been utilized in the circuit of FIG. 8: A resonant frequency of about 5.3 MHz; inductance of the primary and secondary 32, 34 (L1, L2) of about 10 nanohenry and 50 microhenry, respectively; a net capacitance (C+Cs/2) of about 10 pf for the test cell 10; an input current to the secondary of about 40 ma; va initial operating point of about 50 VPP. The Q of the circuit (i.e., the LC value of the secondary 34 and test cell 10) is on the order of 10.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A sensor apparatus for detecting a flow of material along a given path of travel by detecting a change in the dielectric properties of a portion of said path of travel as the material passes therethrough, said apparatus comprising: electrode means disposed adjacent said path of travel and generally defining a capacitor having that portion of the path of travel adjacent thereto as a dielectric portion, such that the passage of material to be detected along the path of travel changes the dielectric constant thereof, thereby changing the capacitance of the capacitor defined by the electrode means; and a sensor circuit comprising a tuned circuit having said capacitor defined by the electrode means coupled in circuit therewith; said sensor circuit further comprising an oscillator circuit driving said tuned circuit at a predetermined frequency,, said predetermined frequency being selected removed from the resonant frequency of said tuned circuit in the absence of said material to be detected by an amount sufficient to cause a change in the voltage across the tuned circuit due to the flow of material along the path of travel to occur substantially entirely within a substantially constant slope, linear region of a pair of voltage-frequency curves characteristic of the response of the tuned circuit in the absence of said material and in the presence of said material respectively; said sensor circuit further including an AM demodulator circuit coupled therewith for developing a sensor circuit output signal at a substantially constant signal level in the absence of material to be detected and for producing a measurable change in said signal level when the material to be detected is present.

2. Apparatus according to claim 1 wherein the material to be detected comprises a plurality of discrete articles passing along the path of travel, and wherein said electrode means comprises a pair of plate-like members, one to either side of the path of travel, wherein said tuned circuit comprises a singly tuned magnetically coupled circuit having a primary and a secondary, said plates being coupled across said secondary and wherein said AM demodulator circuit is responsive to a momentary change in the effective capacitance across said electrodes as one or more discrete articles pass therebetween for causing a corresponding momentary change in the signal level of said sensor circuit output signal.

3. Apparatus according to claim 2, wherein said AM demodulator circuit includes a rectifier circuit coupled with said secondary and a low pass filter circuit coupled with said rectifier circuit.

4. Apparatus according to claim 3 wherein said AM demodulator circuit further includes an amplifier circuit coupled with said low pass filter circuit.

5. Apparatus according to claim 4 wherein said amplifier circuit comprises two input difference amplifier, and further including DC removal circuit means coupled intermediate the low pass filter and the respective ones of the two difference amplifier inputs for removing the DC pedestal of the signal applied to said inputs, for permitting said difference amplifier to respond substantially only to changes in the voltage level of the applied signal due to the passage of material to be detected between the electrodes.

6. Apparatus according to claim 5 wherein said DC removal circuit means comprises a pair of capacitors coupled respectively in series circuit intermediate said low pass filter and the respective inputs of said difference-type amplifier.

7. Apparatus according to claim 3 wherein said rectifier circuit comprises a first diode having a cathode coupled with one end of said secondary, and a second diode having an anode coupled with the opposite side of said secondary, and wherein said low pass filter circuit is coupled across the anode of the first diode and the cathode of the second diode.

8. Apparatus according to claim 5 wherein said low pass filter circuit comprises a capacitor coupled between the anode of the first diode and the cathode of the second diode and resistive means coupled respectively intermediate a common constant voltage reference point and the anode of the first diode and cathode of the second diode respectively for establishing a DC bias point for the secondary and for, together with the capacitor, forming said low pass filter circuit.

9. Apparatus according to claim 6 wherein said AM demodulator circuit further includes an amplifier circuit coupled with said low pass filter circuit.

10. Apparatus according to claim 2 wherein said electrodes are two in number, and comprise a pair of similar, generally rectilinear plates disposed in alignment with each other on opposite sides of said path of travel.

11. Apparatus according to claim 10 wherein said rectilinear plates extend substantially across the cross-sectional dimension of the path of travel in their dimension transverse thereto but are relatively short in their dimension along the path of travel.

12. Apparatus according to claim 10 wherein said plates are relatively flat, planar members.

13. Apparatus according to claim 10 wherein said plates are curved to generally conform to a path of travel having curved boundaries.

14. Apparatus according to claim 10 and further including a generally tubular elongate member defining a portion of said path of travel, said plate-like electrodes being mounted adjacent outer walls of said tubular member at opposite sides thereof.

15. Apparatus according to claim 14 wherein said tubular member is generally rectangular in cross-section.

16. Apparatus according to claim 14 wherein said tubular member is generally circular in cross-section.

17. A sensor circuit for use with a sensor apparatus for detecting a flow of material along a given path of travel by detecting a change in the dielectric properties of a portion of said path of travel as the material passes therethrough, wherein said sensor apparatus responds to the passage of material to be detected along the path of travel by changing its capacitance, said sensor circuit comprising: a tuned circuit, said sensor circuit further comprising an oscillator circuit driving said tuned circuit at a predetermined frequency, said predetermined frequency being selected removed from the resonant frequency of said tuned circuit in the absence of said material to be detected by an amount sufficient to cause a change in the voltage across the tuned circuit due to the flow of material along the path of travel to occur substantially entirely within a substantially constant slope, linear region of a part of voltage-frequency curves characteristic of the response of the tuned circuit in the absence of said material and in the presence of said material respectively; said sensor circuit further including an AM demodulator circuit coupled with the tuned circuit for developing a sensor circuit output signal at a sdubstantially constant level in the absence of material to be detected and for producing a measurable change in said output signal level when the material to be detected is present.

18. A circuit according to claim 17 wherein the material to be detected comprises a plurality of discrete articles passing along the path of travel and wherein said AM demodulator circuit is responsive to a momentary change in the effective capacitance of the sensor as one or more discrete articles pass for causing a corresponding momentary change in the signal level of said sensor circuit output signal.

19. A circuit according to claim 17 wherein said AM demodulator circuit includes a rectifier circuit and a low pass filter circuit coupled with said rectifier circuit.

20. A circuit according to claim 19 wherein said AM demodulator circuit further includes an amplifier circuit coupled with said low pass filter circuit.

21. A circuit according to claim 20 wherein said amplifier circuit comprises a difference amplifier having two inputs, and further including DC removal circuit means coupled intermediate the low pass filter and the difference amplifier inputs for removing the DC pedestal of the signal applied to said inputs for permitting said difference amplifier to respond substantially only to changes in the voltage level of the applied signal due to the passage of material to be detected along the path of travel.

22. A circuit according to claim 21 wherein said DC removal circuit means compises a pair of capacitors coupled respectively in series circuit intermediate said low pass filter and the respective inputs of said difference amplifier.

23. A circuit according to claim 19 wherein said tuned circuit comprises a singly tuned magnetically coupled circuit having a primary and secondary, wherein said rectifier circuit comprises a first diode having a cathode coupled with one side of said secondary and a second diode having an anode coupled with the opposite side of said secondary, and wherein said low pass filter circuit is coupled across the anode of the first diode and the cathode of the second diode.

24. A circuit according to claim 23 wherein said low pass filter circuit comprises a capacitor coupled between the anode of the first diode and the cathode of the second diode and resistive means coupled respectively intermediate a common constant voltage reference point and the anode of the first diode and cathode of the second diode respectively for establishing a DC bias point for the secondary and for, together with the capacitor, forming said low pass filter circuit.

* * * * *